United States Patent [19]

Chen

[11] Patent Number: 4,875,478
[45] Date of Patent: Oct. 24, 1989

[54] PORTABLE COMPRESSION GRID & NEEDLE HOLDER

[76] Inventor: Harry H. Chen, 215 E. Chicago Ave., Chicago, Ill. 60611

[21] Appl. No.: 333,760

[22] Filed: Apr. 5, 1989

Related U.S. Application Data

[63] Continuation of Ser. No. 36,870, Apr. 10, 1987, abandoned.

[51] Int. Cl.$^4$ .............................................. A61B 6/00
[52] U.S. Cl. ................................. 128/303 B; 378/20; 378/37
[58] Field of Search ............ 128/303 B, 749, 751–754; 378/20, 37, 177, 179, 180, 195, 196

[56] References Cited

U.S. PATENT DOCUMENTS

| | | |
|---|---|---|
| 1,370,640 | 3/1921 | Granger . |
| 3,817,249 | 6/1974 | Nicholson . |
| 3,824,397 | 7/1974 | Bauer et al. ........................ 378/180 |
| 4,022,191 | 5/1977 | Jamshidi . |
| 4,259,585 | 3/1984 | Novak et al. . |
| 4,427,005 | 1/1984 | Tener . |
| 4,573,180 | 2/1986 | Summ . |
| 4,580,561 | 4/1986 | Williamson . |
| 4,583,537 | 4/1986 | Derechinsky et al. . |
| 4,583,538 | 4/1986 | Onik et al. . |
| 4,599,738 | 7/1986 | Panetta et al. . |
| 4,691,333 | 9/1987 | Gabriele et al. ...................... 378/37 |

FOREIGN PATENT DOCUMENTS

| | | | |
|---|---|---|---|
| 2352531 | 12/1977 | France .................................. 378/37 |
| 0202452 | 12/1966 | U.S.S.R. ........................... 128/303 B |

OTHER PUBLICATIONS

Price, J. S. and Butler, P. D. *Stereoscopic Measurement in Mammography*, Proc. of the British Inst. of Radiology, p. 901, Nov. 1971.
Bolmgren, Jacobson and Nordenstrom in *Sterotaxic Instrument for Needle Biopsy of the Mamma*, The J. Roentgenol., 129:121–125, Jul. 1977.
Yagen, et al. *Mammographic Needle Localization of Lesions Seen In Only One View*, Amer. J. Roentgenology, 144:911–916, May 1985.
Svane, G., *A Stereotaxic Technique for Preoperative Marking of Non-Palpable Breast Lesions*, Acta Radiologica Diagnosis, 24, (1983) Fasc, 2, pp. 145–151.
TRC Mammotest, brochure, Fischer Imaging Midwest, Inc., 1800 Elmhurst Road, Elk Grove Village, Ill. 60007.
Thomson CGR Stereotix, brochure and Preliminary Users Manual, CGR Skandinaviska ab, Torshamnsgatan 28, Kista, Box 1243, S-163 13, Spanga, Sweden.
Philips Cytoguide, Overall View of System.
Mark 3D Stereographic Breast Biopsy Guide, AB Medide, Promotional Literature.

*Primary Examiner*—Dalton L. Truluck
*Assistant Examiner*—Denise Whelton
*Attorney, Agent, or Firm*—McAulay, Fisher, Nissen & Goldberg

[57] ABSTRACT

A method and apparatus for locating breast lesions in three dimensions and placing the tip of a biopsy needle in the lesion includes a compression apparatus having radiopaque grids on top and bottom compression plates. Two rotated x-ray views are taken, one on either side of the vertical, such that the grids are reproduced on the exposures. The coordinates of the lesions on the grids are plotted as intersecting lines to graphically determine the X, Y and Z coordinates of the lesion. The apparatus also includes a biopsy needle holder and guide which is adjustable according to the graphically determined coordinates and which allows release of the needle from the apparatus while maintaining its position in the lesion.

21 Claims, 4 Drawing Sheets

PORTABLE COMPRESSION GRID & NEEDLE HOLDER

This application is a continuation of application Ser. No. 07/036,870, filed 4/10/87 now abandoned.

BACKGROUND OF THE INVENTION

1. Technical Field:

The invention relates to radiation diagnostics and more particularly to an improved method and apparatus for locating an internal breast lesion along three-dimensional coordinates by radiologic examination and quickly and accurately inserting the tip of a needle in the lesion for performing a biopsy or marking the lesion's location by means of a dye or guide wire.

2. Description of the Prior Art:

Breast cancer is one of the leading causes of death in women in the United States. In 1983, there were 114,000 new cases of breast cancer in this country which represented about 26% of all new cancer cases in women. By far the most useful technique in early detection is mammography, radiological examination of the breast to discover the existence and location of a lesion or "lump". Once a lesion is located, it is then necessary to obtain a tissue sample for examination, or biopsy, so as to determine the nature of the lesion, e.g. benign or malignant.

Generally, the methods available to obtain a tissue sample of the lesion, or cells from the tissue, include surgical excision or needle biopsy and aspiration. Before surgery can be performed, the lesion must be located so that a visual tract can be seen from the surface of the skin to the lesion. Such a tract is generally marked by a thin guide wire placed in the tissue or a blue dye injected into the tissued along the tract.

However, multiple attempts at inserting the needle for placing the wire or dye are invariably required. This is due to the fact that the breast has neither a fixed shape nor reliable constant landmarks other than the nipple. It must be maintained in relatively strict confinement during location of the lesion or, with almost any movement of the patient, it will deform and render meaningless and three-dimensional coordinates for locating the lesion therein. Repeated decompression and recompression exacerbate the difficulties greatly by making it extremely difficult to accurately and precisely reproduce needle placement.

Similarly, needle biopsy and aspiration requires extreme accuracy and several attempts at needle placement is both traumatic for the patient and time consuming. Some attempts have been made at employing compression grids with very limited success. Current compression grids only measure in two dimensions and depth is left to be estimated based on the preliminary mammogram, where the breast was compressed in an orthogonal direction to the direction of needle placement compression.

In attempt to reduce artifacts in the mammogram associated with subject motion and X-ray scattering, compression mammography was developed wherein the breast is held in compression between two plates while an x-ray is taken. Various designs for such a compression apparatus have been developed and some representative examples are illustrated in U.S. Pat. Nos. 4,599,738 to Panetta, et al.; 4,259,585 to Novak, et al.; and 4,573,180 to Summ.

Panetta discloses a wall mounted system which provides for magnified as well as non-magnified compression examination of a female breast for multiple positions while the patient remains seated or standing. Novak discloses an apparatus which holds the breast in compression and has a marking or scale on the upper compression plate which is reproducible on the x-ray film and therefore locates the lesion, but in the X-Y plane only. Summ discloses a motor driven compression apparatus for preparing normal or enlarged x-ray images.

Granger, U.S. Pat. No. 1,370,640, discloses an apparatus for localizing foreign bodies wherein the patient lies on a table having a transparent top and a movable x-ray source therebelow. The x-ray source is moved until the shadow of the foreign body being searched for is located in a small fluorescent area of a screen positioned above the patient. A localizer plate is then slipped between the patient and the table and is positioned so that the shadow is seen lying directly over a cross within a small hole in the localizer plate.

The x-ray source is then moved until the shadow of the foreign body is seen to leave the central area of the cross and assure a similar position with respect to a lateral area of the cross. A pointer on a vertical scale between the fluorescent plate and the vertical plate is then raised until its shadow blends with the shadow of the lateral area of the cross. The pointer now lies on a vertical plane with the foreign body and a small mark can be made on the skin at the cross to indicate the location of the foreign body in the X-Y plane as well as at the end of the pointer to indicate the vertical position of the foreign body.

Only one of these patents, Granger, provides for the three-dimensional location of a foreign body. However, it is clear that the system of Granger has at least two disadvantages when applied to mammography. First there is the affect of even the slightest movement by the patient on the table, which could cause a locating mark to be made in the wrong spot on the skin.

Second, the x-ray source must move in relation to the x-ray film. Dedicated mammography equipment in use today employs an x-ray source which is fixed in a substantially perpendicular relation to the x-ray film. Therefore, the apparatus of Granger could not be employed with available mammography equipment.

Another attempt at location of a breast lesion is described in Price, J. L. and Butler, P. D., *Stereoscopic Measurement in Mammography*, Proc. of the British Inst. of Radiology, p. 901, Nov. 1971. The method employed involves two exposures taken from a superior-inferior position with the x-ray tube displaced 7 centimeters between exposures. These exposures are viewed and aligned together on a mirror stereoscope and then aligned with the lesion. Two parallax readings are taken from which the depth of the lesion is calculated according to formulae described therein. The difficulty of practising this technique with the currently available fixed source equipment is apparent.

Another serious consideration in mammography is the diagnosis of a lesion once located. The best method of forming such a diagnosis is to sample and test, a portion of the tissue from the actual lesion. The obvious aim is to sample the lesion tissue with the least discomfort to the patient. This usually entails a procedure along the lines of a needle biopsy in which a hollow needle is inserted into the tumor or lesion and a sample of the tissue is drawn out, either with the needle after detachment by rotation, or by other means such as aspiration.

A number of devices have been proposed to facilitate needle placement. These are often referred to as stereotaxic devices and are exemplified in U.S. Pat. Nos. 4,583,538 to Onik, et al.; 3,817,249 to Nicholson; 4,580,561 to Williamson; and 4,427,005 to Tener.

Onik, in FIG. 6 and the accompanying text, discloses a device for positioning a biopsy needle in three-dimensions which requires computed tomography to initially locate the lesion. The device of Nicholson is for positioning electrodes in the x-y plane only. Williamson discloses an apparatus employing two parallel compression grids which are used to direct interstitial implants through the breast along a line normal to the plates. Tener discloses a template for controlling the location and placement of needles in a breast in preparation for placing radioactive seeds.

Clearly it is desirable to insert the needle and draw the sample as expeditiously as possible. This requires extreme accuracy both in location of the lesion as well as subsequent placement of the needle, both of which are greatly complicated by the pliancy of the breast. Furthermore, when location of the lesion and placement of the needle are performed in two separate operations, as is suggested by the references above which generally disclose either means for locating the lesion or for placing the needle, the problem is exacerbated greatly.

Attempts have been made to combine the two functions specifically in the area of breast lesions. One such apparatus is marketed under the name TRC MAMMOTEST by Tekniska Röntgencentralen AB, P.O. Box 121, S-183 22 TÄBY, Sweden. The development of the instrument is described by Bolmgren, Jacobson and Nordenstrom in *Stereotaxic Instrument for Needle Biopsy of the Mamma*, The J. Roentgenol., 129:121-125, July 1977 and some of its methods are employed in Svane, G., *A Stereotaxic Technique for Preoperative Marking of Non-Palpable Breast Lesions*, Acta Radiologica Diagnosis, 24, (1983) Fasc. 2, pp. 145-151.

With the MAMMOTEST, the patient lies face down in a prone position on a horizontal platform mounted above the instrument with the involved breast hanging through a hole in the platform and compressed between two plates. Two x-ray exposures through the breast are taken by rotating the x-ray source to plus or minus 15° from the line normal to the center of the film plate. A digital computer is then utilized to compute mathematical expressions for the coordinates of the lesions according to complex formulae set forth and explained in the Bolmgren publication.

Another method of location and needle placement is described in Yagen, et al. *Mammographic Needle Localization of Lesions Seen In Only One View*, Amer. J. Roentgenology, 144:911-916, May 1985. Briefly, the Yagen technique involves a preliminary mammogram taken preferably of a mediolateral view to determine the point of entry for the localization needle, and over which a small adhesive marker is placed. The x-ray source is then rotated 30° without changing the position of the breast. An exposure is made and the depth of the lesion is calculated as 1.73 times the distance measured between the images of the tape marker and the lesion. The mathematical basis for the factor 1.73 is derived in the publication. A needle and subsequently a guide wire are placed based on the point of entry and the calculated depth. As is apparent from an analysis of FIG. 2 of the reference, Yagan makes the assumption that the x-rays emanating from each position of the tube during a given exposure are parallel to one another at approximately 36 inches from the x-ray source. This assumption is not valid. X-rays do not emanate from a point source as parallel rays but rather spread out with increasing distance from the source. This introduces problems of parallax which could seriously affect the accuracy of the Yagan device. Furthermore, there is the problem discussed above relating to the natural pliancy of the breast, in which two exposures are taken while attempting to avoid moving the breast. At no time is compression employed.

In addition to the freestanding MAMMOTEST apparatus, Applicant is aware of two other commercially available units designed to fit onto existing mammography equipment. The first is the STEREOTIX instrument for fine needle biopsy put out by CGR skandinaviska ab, Torshamnsgaten 28, Kista, Box 1243, S-163 13 SPANGA, Sweden. This machine is also a digital computer-based apparatus designed to fit specifically on a Thomson CGR Senographe 500T mammography unit.

The other such machine is the CYTOGUIDE put out by Philips which also requires a digital computer for calculation of the coordinates of the lesion. This unit is designed to fit on a Philips mamography unit.

Both the STEREOTIX and the CYTOGUIDE units utilize the same complex mathematical principles explained in the Bolmgren article with respect to the TRC MAMMOTEST. In both the STEREOTIX and the CYTOGUIDE, the patient may be sitting or standing, the breast is compressed between a compression plate and a breast support/film holder, both of which are suspended above what was the original breast support plate of the mammographic unit to which the STEREOTIX or CYTOGUIDE is attached. However, as with the MAMMOTEST, the breast is held stationary while the x-ray source and film plate are rotated to take two views at plus and minus 15° from the orthogonal to the film plate. In all of the above-described prior art units, symmetry of the two views taken is required for accurate computation of the coordinates of the lesion which, for all practical purposes, must be performed by computer.

TRC MAMMOTEST also provides a removable puncture device which is adjusted to the calculated coordinates and then attached to the compression portion of the apparatus. The puncture device does not allow for removal of the needle from the device while its position in the lesion is maintained. This is a considerable disadvantage in that it severely limits the types of tissue sampling techniques available to the physician. Both the STEREOTIX and the CYTOGUIDE also include a puncture apparatus, both of which suffer from the same short-coming as the MAMMOTEST.

There are a number of other disadvantages associated with these commercially available prior art devices. The TCR MAMMOTEST is a very large freestanding device dedicated to the breast lesion localization and needle placement as described. A substantial amount of expensive hospital floor space is therefore required for this very costly machine despite its extremely limited function. Further, as the Bolmgren article notes, patients are chosen who have palpable or non-palpable lesions and who require further cytological study. (Bolmgren, page 121, Procedure). The original, traditional mammogram, in which the lesion is initially identified and preliminarily located, is taken with the patient in a sitting position. However, the MAMMOTEST requires that the patient be prone and face down. Therefore, breast architercture surrounding the lesion may well change rendering visualization on the MAMMOTEST very difficult.

It should be noted that the other two devices, the STEREOTIX and the CYTOGUIDE, are both designed to function with a particular mammography unit and therefore their use is quite limited. Further, even if the facility looking to add such a device already has the appropriate mammography unit, the Applicant is advised that the attachments themselves are extremely costly, in the vicinity of $50,000.00 for the CYTOGUIDE and $60,000.00 for the STEREOTIX.

As noted above, all three units require the use of a digital computer for calculation of the coordinates of the lesion. Besides the expense, this requirement also increases the possibility of inaccuracy or even total disablement of the apparatus based on the computer failure.

All three of the units also require exact positioning of the x-ray source at plus and minus 15° for accurate calculation of coordinates. Even slight misalignment may substantially affect the computations.

Finally, none of these devices allow for release of the needle from the positioning apparatus once it is advanced into the lesion without withdrawing the needle from the lesion. Therefore, only the tissue directly in line above, through and below the lesion can be sampled.

Applicant is aware of one other existing unit but does not know if the unit is commercially available. It is called the MARK 3D Stereographic Breast Biopsy Guide from AB MEDIDE and does not appear to employ the novel apparatus and method described and claimed hereinafter.

SUMMARY OF THE INVENTION

The invention provides a portable compression grid and needle holder for radiologic location of breast lesions along three-dimensional coordinates and needle placement in the lesion to facilitate cytological sampling, examination and removal thereof. The invention includes means for mounting the apparatus on conventional mammography units, a top breast compression plate having a cut-out area or portion and a bottom breast support plate, each plate having a radio-opaque grid or scale therearound. The support plates are adjustably connected to one another by a vertical support or spine having a scale thereon for measuring in the Z, or vertical, direction.

The apparatus is rotatably connected to the mounting means to facilitate taking two x-ray exposures, one on either side of a line normal to the plane of the x-ray film on mammography units having a stationary x-ray source.

When the two views are taken, the radio-opaque grids from the top and bottom plates will be reproduced on the film around the lesion. This allows simple coordinates to be read directly from the film. Intersecting lines and points can be drawn manually on graphs corresponding to the grids on the plates according to the coordinates read from the film. One graph locates the lesion in the X-Z plane and the other locates the lesion in the Y-Z plane.

The apparatus also includes an adjustable needle holder and guide assembly mounted on the upper support plate which is readily adjustable in three-dimensions and immediately facilitates the insertion of a needle directly and accurately into the lesion. In addition, the needle holder assembly allows for removal of the needle from the assembly while maintaining the needle point in the lesion to facilitate aspiration of tissue as well as aspiration of tissue in the immediate area of the lesion by allowing movement in three dimensions.

The exposures may be taken with the patient in a sitting or standing position and the breast need never be removed from the apparatus from the time that the first exposure is taken until the tissue sampling needle is in place, a period which may well not be greater than a few minutes. This alleviates the problem of a two part procedure where the architecture and dimensions of the tissue surrounding the lesion may not remain constant by eliminating the need for multiple location and/or needle placement.

DESCRIPTION OF THE PREFERRED EMBODIMENTS

Figures 1, 1A, 2:
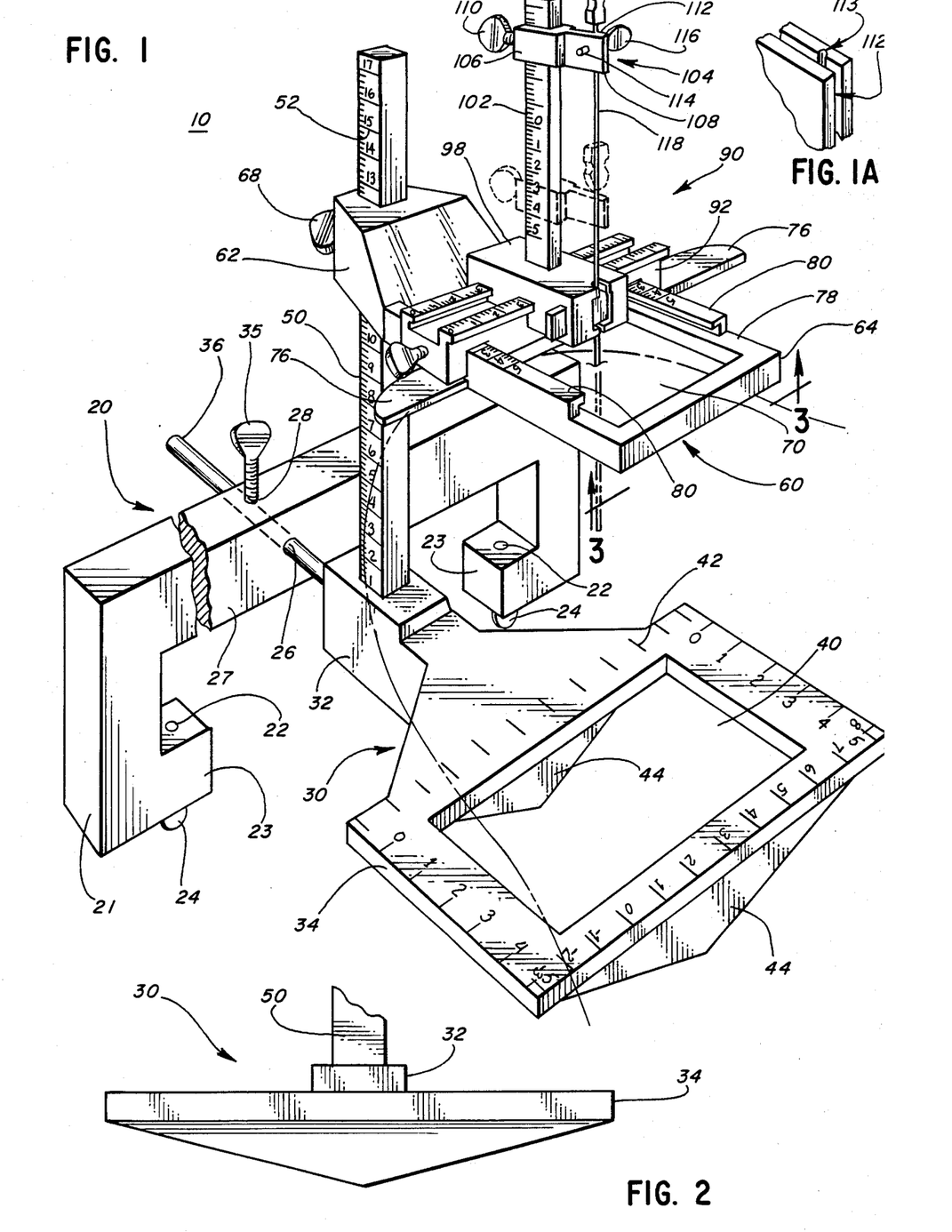
FIG. 1 is a perspective view of the apparatus embodying the invention looking toward the front end thereof.
FIG. 1A is a fragmentary perspective view of the needle holder portion of the needle hub positioner assembly of the apparatus of FIG. 1 without a needle placed therein.
FIG. 2 is a fragmentary front view of the bottom breast support plate of the apparatus of FIG. 1.

Referring to the drawings in which like structures are labelled with like reference numerals, FIG. 1 represents the apparatus embodying the invention designated generally by the reference numeral 10. The apparatus 10 includes a mounting bracket assembly 20 for mounting device 10 on a table, film holder, etc. of an existing mammography unit. Assembly 20 includes a C-bracket 21 having threaded holes 22 in the top and bottom tails 23 of the bracket 21 for thumbscrews 24. Bracket 21 also has a transverse hole 26 through the longest section 27 of the bracket 21 and a threaded hole 28 through section 27 approximately normal to and intersecting hole 26.

The device 10 has a bottom breast support plate assembly 30 having a neck portion 32 and a radiolucent support portion 34. Neck portion 32 has a bar 36 extending out from the rear portion thereof which is inserted through the hole 26 on the bracket assembly 20 and maintained in a given position by thumbscrew 35 to removably and rotatably secure support assembly 30 to mounting bracket assembly 20. The bottom breast support plate 30 includes a spine or support 50 which extends vertically from the top of neck portion 32 and has a scale 52 engraved, printed, or otherwise permanently affixed thereto along its length.

Figure 3:
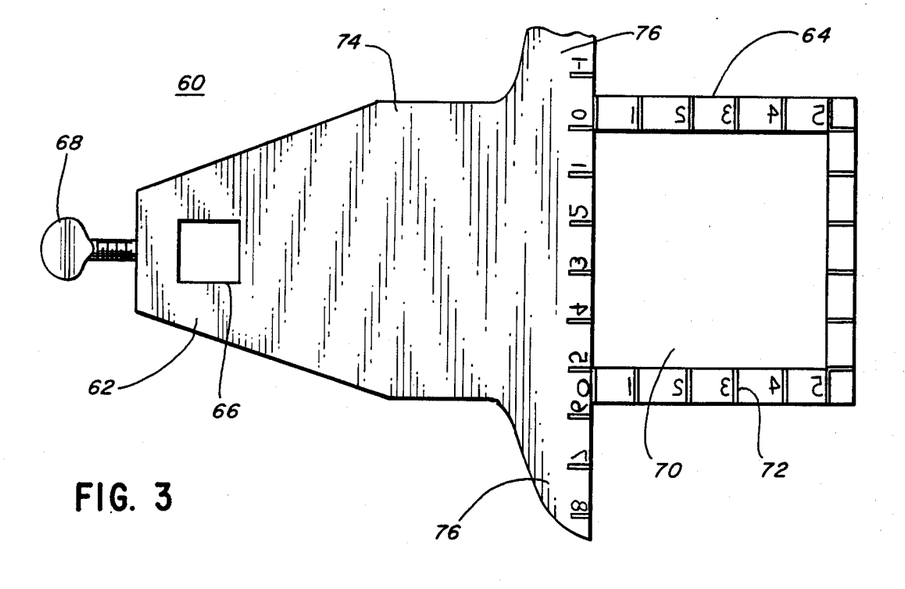
FIG. 3 is a bottom plan view of the top breast support plate of the apparatus of FIG. 1.

A top compression plate assembly 60 having a neck portion 62 and a radiolucent compression portion 64 is adjustably mounted on the spine 50. This may be achieved by the use of a square hole 66 through the neck portion 62 of compression plate assembly 60 in conjunction with a thumbscrew 68 as illustrated in FIGS. 1 and 3, or any other suitable means.

Device 10 includes a needle holder and guide assembly 90 adjustably mounted on the compression plate assembly 60, which will be described in detail hereinafter.

Referring now to FIGS. 1 and 2, the bottom breast support plate assembly 30 may include a cut-out area 40 which provides a more stable securing of the breast tissue. A radio-opaque or a x-ray absorbing grid 42 is marked off around the periphery of support assembly 30 in any convenient units, such as centimeters. The grid may be applied by any suitable method. Cut-out area 40 also eliminates at least one layer of material through which the radiation must pass, and therefore tends to provide a clearer image.

Bottom plate assembly 30 includes two matching triangular legs 44 which serve to steady the apparatus when each of the two x-ray exposures are taken, as will be described in detail with respect to the method of the invention.

Vertical spine 50 may be separately manufactured and attached to neck portion 32 of bottom assembly 30 by any suitably method. Spine 50 may also be manufactured as one piece with neck and support portions 32 and 34, such as by casting or molding. The vertical scale 52, should be marked in units compatible with those of grid 42, and, when a breast is properly inserted in the device 10, provides a convenient reference for the thickness of the breast in compression.

Referring to FIGS. 1 and 3, top compression plate assembly 60 has a neck portion 62 and a compression portion 64. Top assembly 60 is attached to spine 50 such as by providing a square hole 66 through neck portion 62 which is dimensioned to fit snugly over spine 50 as shown. In this way compression portion 64 is maintained in substantially parallel relation to support portion 34 of bottom assembly 30. Compression assembly 60 is maintained at a desired vertical level with respect to bottom assembly 30 by any convenient method such as thumbscrew 68.

Compression plate assembly 60 includes a cut-out portion or area 70 which, when assembly 60 is mounted on spine 50, is essentially in line with bottom support assembly 30. A radio-opaque or radiation absorbing grid 72 is applied around the periphery of area 70 preferably on the under side 74 of assembly 60 facing grid 42 on bottom assembly 30. Grid 72 is marked in the same units as grid 42. Because of their radio-opaque nature, both grids 42 and 72 will be reproduced on x-ray exposures taken with the apparatus of the invention interposed between the x-ray source and the film. In this manner, it is assured that vertical and horizontal lines superimposed on the exposed films which intersect in the center of the lesion being located will also intersect both the ordinate and the abscissa of each of the grid reproduced in the films.

Further, compression assembly 60, as illustrated, has on its under side 74 two laterally extending arms or side leaves 76. Arms 76 have marked thereon extensions in both directions of the X scale of grid 72. These arms with extensions serve to substantially reduce the possibility that a lesion in a rotated x-ray view will be located near the periphery of top plate 64 and therefore off the scale.

On its top side 78 (FIG. 1), compression plate assembly 60 includes a pair of rails 80 along the lateral sides thereof in the Y-direction having ruled calibrations thereon which are in units coinciding with those of grids 42 and 72 and vertical scale 52. Rails 80 function with respect to needle holder 90 as will be explained.

Figures 4, 5:
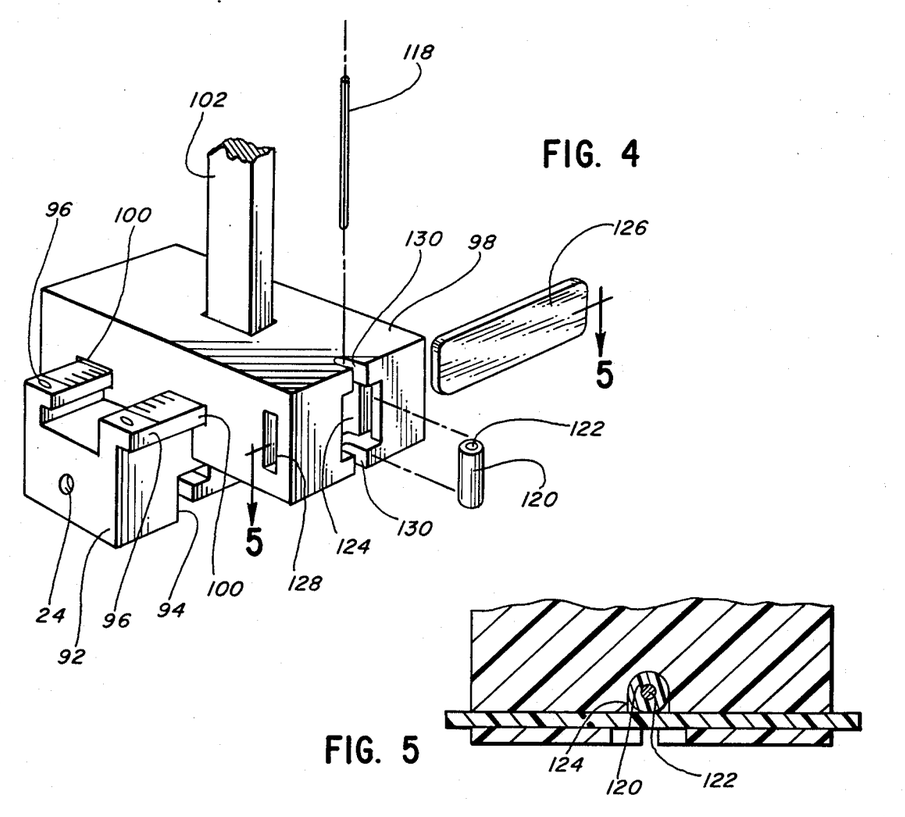
FIG. 4 is a fragmentary exploded perspective view of the base portion of the needle holder and guide assembly of the apparatus of FIG. 1.
FIG. 5 is a partial section view of the base portion of the needle holder and guide assembly along line 5—5 of FIG. 4, however, with the needle, bushing and rectangular plate for maintaining the needle in the assembly in place.

Referring to FIGS. 1, 4 and 5, needle holder and guide assembly 90 includes a base 92 having a pair of transverse parallel channels 94 (FIG. 4) therethrough which are spaced and dimensioned to fit and slide reciprocally over rail 80 in the Y-direction as seen in FIG. 1. Base 92 also may include a threaded hole 24 for a thumbscrew (not shown in FIG. 1) or any other appropriate means to maintain base 92 at a given location on the Y scale of rail 80.

Base 92 has two parallel rails 96 similar to rails 80. but extending longitudinally along the top base 92 in the X direction. These rails 96 also have ruled calibrations thereon having units corresponding to the ruled calibrations on rails 80, grids 42 and 72 and vertical spine 50. The cross-sectional L-shape of rails 80 and 96, as well as channels 94, is preferred so as to preclude reverse alignment of the various parts of the assembly 90. However, it will be appreciated that the invention is not limited in this regard and any suitable cross-sectional shape may be employed.

Needle holder assembly 90 also includes a transverse sliding base 98 having parallel channels 100 therethrough which are spaced and dimensioned to fit and slide reciprocally over rails 96 in the X-direction as apparent in FIGS. 1 and 4. A threaded hole and thumbscrew (not shown) or any other appropriate means may be provided, such as at the rear of sliding base 98, to maintain it at a given position along the X scale of rails 96 on base 92.

Needle holder assembly 90 is further provided with a ruled vertical rod 102 similar to vertical spine 50 but smaller and extending from the top of sliding base 98. Again, the units of the calibrations should coincide with those on rails 80 and 96, spine 50, and grids 42 and 72.

Vertical rod 102 has adjustably mounted thereon a needle hub positioner assembly 104 having a neck portion 106 and a needle holder portion 108. Neck portion 106 has a hole therethrough through with vertical rod 102 extends. Hub positioner assembly 104 may be releasably fixed at a given position along the ruled rod 102 by thumbscrew 110.

Needle holder portion 108 has a longitudinal split 112 therethrough with a transverse threaded hole 114 and thumbscrew 116 for maintaining a biopsy needle 118 therein as shown in FIG. 1. At least one of the leaves of holder portion 108 has a vertical groove 113. A needle 118 is chosen of a length such that the tip just meets the surface of the breast when the breast is compressed in the apparatus and the neck portion 106 of the needle holder assembly 90 is at the zero position on the vertical scale of rod 102.

Further means for support and guidance of needle 118 are provided in the front portions of transverse sliding 98 as illustrated best in FIGS. 4 and 5. A sterile bushing or hub 120 is provided having a lumen or hole 122 through which the shaft of needle 118 fits comfortably but not so loose as to allow lateral movement. Bushing 120 is inserted in a cavity 124 in the front of sliding base 98. In this way, hole 122 in bushing 120 is aligned with groove 113 to maintain needle 118 in position orthogonal to the plane of grid 72. Cavity 124 is dimensioned to allow the insertion of hub 120 along with a tab 126 which is inserted into a transverse slot 128 through base 98 and cavity 124 to keep bushing 120 in cavity 124. Sliding base 98 is also provided with a vertical slot 130 approximately along the longitudinal center plane of vertical rod 102 and further dimensioned to secure the vertical position of the bushing 120 and to allow the shaft of needle 118 to pass therethrough and through the lumen 122 of bushing 120 when the needle 118 is held in needle holder portion 108 of assembly 90.

The apparatus 10 has a number of advantages over, and alleviates virtually all of the major disadvantages of, the prior art. It fits on most, if not all, existing mammography units, including the Thomson CGR Senographe 500T and the Philips Mammographic units. Also, it is entirely mechanical in its construction and use. Therefore, it is significantly less expensive to manufacture and acquire.

The method and apparatus embodying the invention preferably may be employed after the existance and approximate location of a lesion has been ascertained, such as by traditonal, preliminary mammography. This may be done by simply loosening thumbscrews 24 and removing the apparatus 10. In such a case, the preliminary results will indicate whether a cranial-caudal or medial-lateral compression of the breast will provide the best approach. The apparatus 10 can then be installed and adjusted on bar 36 appropriately for either the cranial-caudal or medial-lateral approach.

The preferred method for utilizing the apparatus 10 is as follows.

1. The breast to be examined in inserted between bottom breast support plate assembly 30 and top compression assembly 60. The lesion is placed approxiamtely within the boundaries of the cut out area 70 of the top compression plate assembly. Top assembly 60 is lowered manually along vertical spine 50 to a point where the breast is comfortably compressed between the assemblies 30 and 60. Top assembly 60 is maintained in this compressed position throughout the location and needle placement by tightening thumbscrew 68.

2. Thumbscrew 35 is kept loose while the entire device 10 with the breast compressed therein is rotated to either the right or the left of a line normal to the film plate until one side or the other of triangular legs 44 rests flush on the x-ray film holder. It should be noted that the particular angle of the sides of legs 44, and therefore the angle of inclination of device 10, is not crucial to the invention because of the particular method employed for determining the coordinates of the lesion which is set forth further below. Similarly, it is not required that each side of legs 44, and therefore the angles at which the device 10 leans to either side of the vertical when the two exposures are taken, be the same for the same reason. The angular sides of legs 44 are provided primarily for steadying the apparatus 10 while the film is being exposed.

3. Thumbscrew 35 is tightened and the first x-ray film is exposed.

4. Thumbscrew 35 is loosened and the device 10 is rotated to the opposite side of the normal until the opposite side of legs 44 is flush with the film holder. Thumbscrew 35 is tightened and the second x-ray film is exposed.

5. The two x-ray films are processed and will look approximately like FIGS. 6 and 7. In each of these figures, the more compact, square scale represents a reproduction on the film of radio-opaque grid 72 on the underside 74 of top compression plate assembly 60. The broader, more rectangularly extended scales in each of FIGS. 6 and 7 represents the reproduction of radio-opaque grid 42 on support portion 34 of bottom support assembly 30.

The coordinates of the lesion on the grids 42 and 72 is read from each of the two films by first drawing perpendicular lines representing an X and a Y axis (or placing an appropriate transparency thereover) on the two films. For purposes of illustration, the scale representing grid 72 on top assembly 60 will be designated T for top and X and Y coordinates on this scale will be designated $X_t$ and $Y_t$. Similarly, the scale representing grid 42 on bottom assembly 30 will be designated B for bottom and the X and Y coordinates on this scale will be designated $X_b$ and $Y_b$. The values read from FIG. 6 will be further designated $X_{t1}$, $Y_{t1}$, and $X_{b1}$, $Y_{b1}$, where the subscript 1 repreents the first rotated view.

Figure 6:
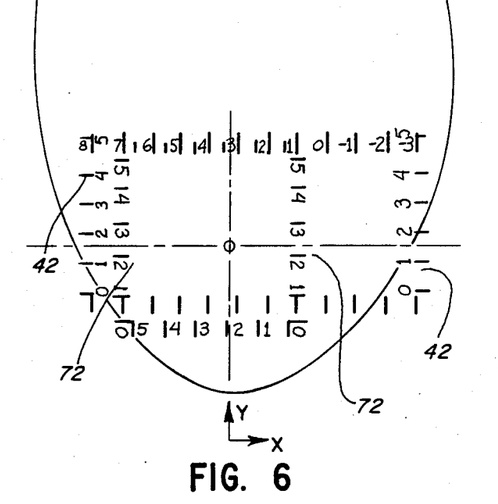
FIG. 6 is an example of an x-ray exposure of a breast with lesion taken on the apparatus of the invention.

In FIG. 6, the vertical line drawn through the lesion intersects the horizontal X scales at $X_{t1} = 2$ and $X_{b1} = 3.3$. The horizontal line drawn through the lesion intersects the vertical Y scales at $Y_{t1} = 2.2$ and $Y_{b1} = 1.5$.

Figure 7:
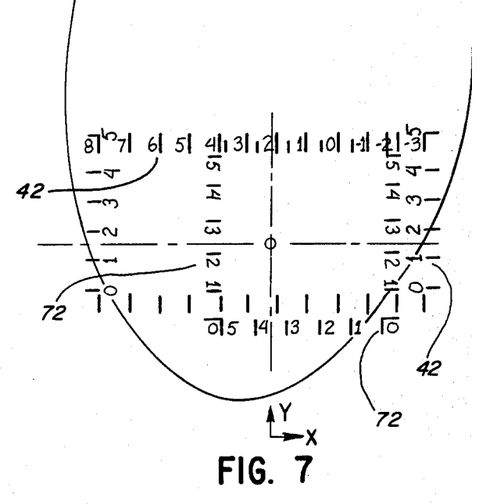
FIG. 7 is an example of another x-ray exposure of the breast of FIG. 6 taken on the apparatus of the invention after rotating the apparatus to the opposite side of the plane normal to the film.

Similar readings in FIG. 7 yield the following values for the second rotated view represented by the subscript 2.

$X_{t2} = 3.4$
$X_{b2} = 2.2$
$Y_{t2} = 2.25$
$Y_{b2} = 1.5$

6. Using the values determined in step 5 for $X_{t1}$, $X_{b1}$, $X_{t2}$ and $X_{b2}$, and the thickness of the compressed breast which is read off the vertical scale 52 on spine 50, the X and Z coordinates of the lesion are quickly and accurately graphically determined as follows with reference to FIG. 8.

Figure 8:
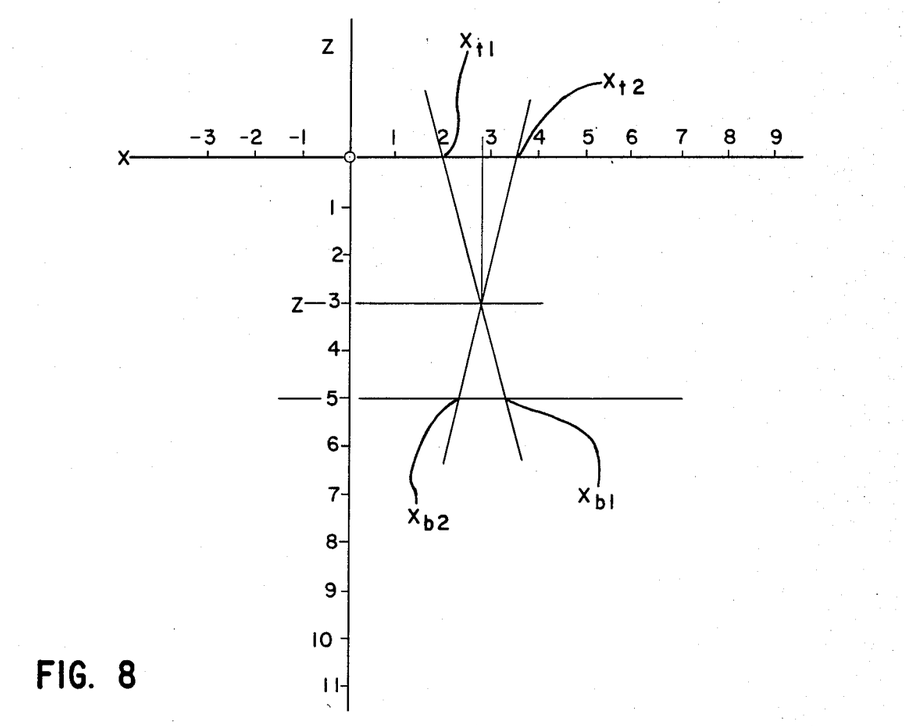
FIG. 8 illustrates the first graphical determination in the location of the lesion of FIGS. 6 and 7, in the X-Z plane, according to the method of the invention.

A graph is prepared previously having X and Z as the abscissa and ordinate respectively and a lower line parallel to the X axis at the number corresponding to the thickness of the compressed breast read from scale 52 on spine 50, and which is ruled in the same units as grids 42 and 72, vertical scale 50, etc. Points $X_{t1}$ and $X_{t2}$ are marked along the X scale. Points $X_{b1}$ and $X_{b2}$ are marked along the lower horizontal line. The intersection of lines $X_{t1}$-$X_{b1}$ and $X_{t2}$-$X_{b2}$ will be the x,z coordinate of the lesion. A horizontal line and a vertical line drawn through the intersection of these same two lines shows that the X coordinate of the lesion is X=2.8, and the z coordinate is z=3.

Figure 9:
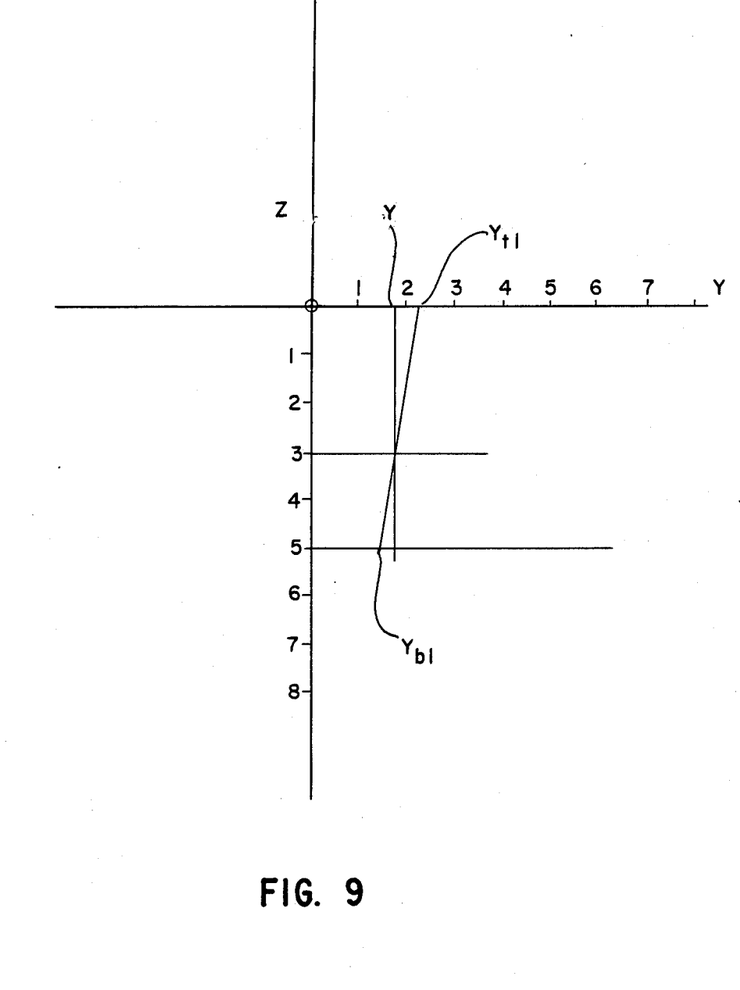
FIG. 9 illustrates the second graphical determination in the location of the lesion of FIGS. 6 and 7, in the Y-Z plane, according to the method of the invention.

9. Using $Y_{t1}$, $Y_{b1}$, and Z, determined in step 8, a vertical line drawn through the intersection of the horizontal line at Z=3 and line $Y_{t1}$-$Y_{b1}$ shown that the y coordinate of the lesion is Y=1.75.

10. Once the coordinates of the lesion are determined as X=2.8, Y=1.75 and Z=3, the needle position is set by sliding base 98 along rails 96 to an X position of 2.8, sliding base 92 along rails 80 to a Y position of 1.75. A needle 118 is then placed in holder portion 108 of holder and guide assembly 90, through lumen 122 of hub 120, thumbscrew 116 is tightened, thumbscrew 110 is loosened and needle 118 is advanced into the lesion by advancing neck portion 106 the specified distance down the Z scale, i.e. to Z=3, on ruled vertical rod 102 and into the breast. Once neck portion 106 is in position, the tip of the needle 118 is in the center of the lesion. Thumbscrew 110 is then tightened. If desired, two x-ray exposures may be obtained at different rotation of the device 10 to confirm the position of the needle tip.

At this point, a number of options are available to the clinician. For example, a guide wire may be threaded through the needle bore and left in place as the needle is withdrawn. Alternatively, a dye such as methylene blue may be injected into the needle as it is withdrawn.

If cytological examination is desired, the needle 118, once placed in the breast, may be marked by such as sterile tape approximately 1 cm above the skin level. The needle may then be released from needle holder portion 108 of holder and guide assembly 90. This is quickly accomplished by loosening thumbscrew 116 which allows needle 118 to be removed from longitudinal split 112 in holder portions 108. Next, tab 126 is withdrawn to either side from transverse slot 128 which allows needle 118 surrounded by hub 120 to be withdrawn from cavity 124.

The clinician may then, for example, attach a 20 ml syringe to the needle 118 and apply and maintain appropriate vacuum to aspirate a sample of the cells from the lesion. With a simple back and forth motion, the clinician can sample the tissue for a one centimeter radius surrounding the center of the lesion.

11. The needle is removed from the breast and the compression released by loosening thumbscrew 68 and raising top compression plate assembly 60.

The present invention provides a method and apparatus for locating soft tissue, and particularly breast lesions along three-dimensional coordinates and accurately placing a needle in the lesion which is far simpler to use and less expensive to manufacture than those of the prior art. The present method and apparatus is also faster, easier, less complicated, totally mechanical and therefore, less susceptible to breakdown and requires only minimal training for operation when compared to the prior art.

The method and apparatus of the invention may be practised other than specifially as described without departing from the spirit and scope of the invention as defined in the appended claims.

I claim:

1. A portable compression apparatus for radiologically and graphically locating breast lesions along three dimensional coordinates to facilitate cytological examination and treatment thereof, comprising:

means for mounting said apparatus on the film cassette holder plate of a dedicated mammography unit, a top radiolucent compression plate having a cut-out area and a first rectilinear grid scale around the periphery of said cut-out area, a bottom radiolucent support plate having a second rectilinear grid scale around the periphery thereof, said bottom plate being rotatably and removably connected to said mounting means, first means for supporting said top plate and for adjustably positioning said top and bottom plates one relative to the other on either side of said breast; said first and second grid scales constructed and arranged to enable formation of corresponding grid scales on the resulting radiograph, which corresponding grid scales, in conjunction with the representation of the lesion also on said radiograph facilitate subsequent direct graphical representation of the location of said lesion relative to said coordinates within said breast, a needle holder and guide assembly adapted to hold a needle for inserting the tip thereof into the lesion, said assembly being adjustable in its position relative to the lesion to enable accurate and reliable insertion of said tip, means providing support and guidance for said needle along two spaced points of the needle to prevent deflection thereof during insertion of said needle tip, said needle holder assembly including first parallel rails on said top plate having calibrations thereon for adjusting the position of said assembly in the Y direction, a first sliding base mounted transversely on said first rails, said first base having second parallel rails mounted longitudinally thereon and having calibrations thereon for adjusting the position of said assembly in the X direction; a second sliding base mounted transversely on said second rails, and second base having a rod extending vertically therefrom, said rod having calibrations and a slidable needle holder thereon, said calibrations and slidable needle holder for adjusting the position of said assembly in the Z direction; said second sliding base including a releasable bushing having a lumen through which said needle extends, said bushing and said slidable needle holder providing support and guidance for said needle, said second base and said needle holder also permitting release of said needle from said apparatus while maintaining said needle tip at said location.

2. The compression plate structure of claim 1 wherein said grid scale and said calibrations are all marked in the same units of measure.

3. The method of locating a breast lesion using an x-ray source comprising:

taking a first radiograph of a breast at a first position relative to the x-ray source, wherein said breast is positioned between first and second compression plates having first and second sets of radio-opaque locating grids thereon respectively to provide a first radiograph of the lesion, said first radiograph having a picture of said first and second sets of locating grids thereon, taking a second radiograph of the same breast at a second position relative to said x-ray source wherein said breast is positioned between said first and second compression plates having said first and second sets of locating grids thereon, to provide a second radiograph of the lesion, said second radiograph having a picture of said first and second sets of locating grids thereon, the position of said breast between said plates being substantially the same in said step of taking said second radiograph as it is in said step of taking said first radiograph, measuring a distance between said first and second sets locating grids when the compressed breast is there-between, said first set of locating grids defining a first plane, the central axis of the x-ray when taking said first radiograph having a first angle to said first plane, the central axis of said x-ray when taking said second radiograph having a second angle to said first plane, said first and second angles being substantially different, and analyzing the position of said lesion in said first and second radiographs relative to coordinates of said first and second grids in each of said radiographs to provide a location of said lesion in three dimensional space.

4. The method of claim 3, wherein said second set of locating grids defines a second plane, said first and second planes being parallel to one another, and wherein said step of measuring is of the distance along a line perpendicular to said first and second planes.

5. The method of claim 4 wherein said central axes of said x-ray beams in said first and second positions intersect.

6. The method of claim 4 wherein:

said first and second sets of locating grids each have respective dual spaced apart x-axes and dual spaced apart y-axes, said x and y axes constituting perimeter coordinates, and y-axes of said first locating grid being parallel to said y-axes of said second locating grid and said x-axes of said first locating grid being parallel to said x-axes of said second locating grid, and said step of analyzing includes the graphical representation of four planes, each of which includes the lesion and the x-ray source, each of said planes being parallel to one of said axes of said grids.

7. The method of claim 6 wherein said step of analyzing includes the step of:

determining at said first position a first lesion line defined by the intersection of a first plane in space parallel to said x-axes and a second plane in space parallel to said y-axes, said first and second planes both passing through the x-ray source and the lesion, determining at said second position, a second lesion line defined by the intersection of a third plane in space parallel to said x-axes and a fourth plane in space parallel to said y-axes, said third and fourth planes both passing through the x-ray source and the lesion, and determining the position of said lesion by the intersection of said first and second lesion lines.

8. The method of claim 7 wherein said x-ray source in said first and second positions is in the same x-z plane and wherein said distance between said first and second sets of locating grids constitutes a distance along a z-axis, and further comprising the steps of:

projecting said first and second lesion lines on a x-z plane and determining the x and z coordinates of said lesion by the intersection of said projected lesion lines on said x-z plane, and projecting at least one of said first and second lesion lines on a y-z plane and determining the y coordinate of said lesion by the intersection of (a) a line parallel to said y-axis intersecting the z-axis at said z coordinate and (b) said one of said projected lesion lines.

9. The method of claim 8 wherein said central axes of said x-ray beams in said first and second positions intersect.

10. The method of claim 4 further including the step of placing a needle tip in said breast lesion.

11. The method of claim 10 further comprising the steps of adjusting said needle after placing said tip and advancing said needle after adjustment into said breast.

12. The method of claim 11 further comprising the step of releasing the needle from the compression plate apparatus while maintaining said needle tip in said breast lesion.

13. Apparatus for locating a breast lesion using an x-ray source comprising:

first and second spaced apart compression plates having first and second sets of radio-opaque locating grids thereon respectively, and mounting means for mounting said plates to a mammography unit and for holding said plates spaced apart from one another when so mounted, said mounting means including means to adjust the distance between said plates, and means for measuring the distance between said plates when said plates are mounted by said mounting means to a mammography unit.

14. The apparatus of claim 13 wherein:

said first set of locating grids defines a first plane and said second set of locating grids defines a second plane, and wherein said mounting means is adapted to hold said plates on a mammography unit such that said first plane and said second plane are held parallel to one another.

15. The apparatus of claim 14 wherein: said first and second sets of locating grids each consist of perimeter scales.

16. The apparatus of claim 15 wherein said first plate is a top plate and is formed with a central cut-out area therein.

17. The apparatus of claim 16 wherein said first locating grid is on the lower surface of said top plate and wherein said second locating grid is on the upper surface of said second plate.

18. The apparatus of claim 16 further comprising: a needle holder and guide assembly adjustable mounted to said top compression plate.

19. The apparatus of claim 17 further comprising a needle holder and guide assembly adjustable mounted to said top compression plate.

20. The apparatus of claim 18 further including releasing means for releasing said needle from said guide assembly.

21. The apparatus of claim 18 wherein said needle holder and guide assembly comprises:

a sterile bushing for engaging the tip ends of a needle to the needle, said sterile bushing being removable mounted to said top compression plate at a position above said top plate, and a keeper for holding said bushing at said top plate, said keeper having a first state which holds said bushing in a predetermined position at said top plate and a second state which permits an operator to release said bushing from said top plate and to permit operator aspiration of tissue from a predetermined zone adjacent to a lesion.

* * * * *